United States Patent
Fukumoto

(10) Patent No.: US 11,786,280 B2
(45) Date of Patent: Oct. 17, 2023

(54) TREATMENT TOOL

(71) Applicant: Teijin Nakashima Medical Co., Ltd., Okayama (JP)

(72) Inventor: Jyunichi Fukumoto, Kobe (JP)

(73) Assignee: TEIJIN NAKASHIMA MEDICAL CO., LTD, Okayama (JP)

( * ) Notice: Subject to any disclaimer, the term of this patent is extended or adjusted under 35 U.S.C. 154(b) by 0 days.

(21) Appl. No.: 17/098,578

(22) Filed: Nov. 16, 2020

(65) Prior Publication Data
US 2021/0077164 A1 Mar. 18, 2021

Related U.S. Application Data

(63) Continuation of application No. PCT/JP2019/019647, filed on May 17, 2019.

(30) Foreign Application Priority Data

May 17, 2018 (JP) .................................. 2018-095326

(51) Int. Cl.
*A61B 17/80* (2006.01)
*A61B 17/74* (2006.01)
*A61B 17/68* (2006.01)

(52) U.S. Cl.
CPC ........ *A61B 17/8004* (2013.01); *A61B 17/744* (2013.01); *A61B 2017/681* (2013.01)

(58) Field of Classification Search
CPC ... A61B 17/681; A61B 17/746; A61B 17/809; A61B 17/8004; A61B 17/8061; A61B 17/8085
See application file for complete search history.

(56) References Cited

U.S. PATENT DOCUMENTS

| 5,797,916 A * | 8/1998 | McDowell | A61B 17/842 |
| | | | 606/297 |
| 9,662,218 B2 * | 5/2017 | Grotz | A61L 27/54 |
| 10,835,301 B1 * | 11/2020 | Paranjpe | A61B 17/809 |
| 2009/0012569 A1 * | 1/2009 | Dall | A61B 17/8085 |
| | | | 606/280 |
| 2009/0198277 A1 * | 8/2009 | Gordon | A61B 17/8076 |
| | | | 606/279 |

(Continued)

FOREIGN PATENT DOCUMENTS

| EP | 0 934 731 A1 | 8/1999 | |
| EP | 2117452 B1 * | 7/2016 | ............. A61B 17/74 |

(Continued)

OTHER PUBLICATIONS

International Search Report for PCT/JP2019/019647 dated Jul. 16, 2019.

*Primary Examiner* — Anu Ramana
(74) *Attorney, Agent, or Firm* — Sughrue Mion, PLLC

(57) ABSTRACT

The present disclosure provides a treatment tool cable of satisfactorily treating long tubular bone fractures, such as femoral trochanteric fractures and subtrochanteric fractures. The treatment tool comprises an elastic plate 2 that has a curved shape or that can be curved, the plate comprising at least one pressing portion 20 that is provided at one end in the width direction of the plate and that presses the trochanter 103 of the femur 100 from the posterior side by a restoring force that is generated by deformation of widening the curvature.

8 Claims, 11 Drawing Sheets

(56) References Cited

U.S. PATENT DOCUMENTS

2015/0182266 A1    7/2015   Jakob et al.
2017/0079701 A1    3/2017   Geldwert

FOREIGN PATENT DOCUMENTS

| JP | 2010-050252 A | 3/2010 |
| JP | 2016-152861 A | 8/2016 |
| JP | 2018-029709 A | 3/2018 |

\* cited by examiner

TREATMENT TOOL

BACKGROUND OF THE INVENTION

Technical Field

The present disclosure relates to a treatment tool for use as an implant or surgical instrument in treating fractures of long tubular bones, such as humerus, radius, ulna, femur, tibia, and fibula; for example, femoral trochanteric fractures or subtrochanteric fractures, proximal humerus fractures, or long tubular bone diaphysis fractures.

Background Art

For example, as a therapeutic method of osteosynthesis for femoral trochanteric fractures and subtrochanteric fractures, fixation surgery using an intramedullary nail (intramedullary fixation) has been known.

In the intramedullary fixation method, after a metal intramedullary nail is inserted into the medullary cavity of the femur, a lag screw is inserted diagonally upward from the lateral surface of the femur toward the bone head so as to penetrate the intramedullary nail, and the intramedullary nail is fixed to the diaphysis by means of fixation bolts to thereby fix bone fragments separated by a fracture (see, for example, Patent Literature (PTL) 1).

CITATION LIST

Patent Literature

PTL 1: JP2010-050252A

BRIEF SUMMARY OF THE PRESENT DISCLOSURE

Technical Problem

Femoral trochanteric fractures and subtrochanteric fractures are often accompanied by a posterolateral defect, which is a separation of the posterolateral portion of the trochanter from the main bone due to additional fracture on the lateral surface of the trochanter. However, if the conventional intramedullary fixation method as described above is used to treat a femoral trochanteric fracture or the like that is accompanied by a posterolateral defect, posterolateral bone fragments separated by the posterolateral defect are not fixed to the main bone, and the femoral trochanteric fracture or the like is thus treated in an unstable state. This unstable state, in which the posterolateral bone fragments are not fixed to the main bone, causes complications such as bone head rotation, prolonged fusion, and cutout during the treatment of femoral trochanteric fracture or the like. This inhibits bone fusion in femoral trochanteric fractures or the like. Therefore, the conventional intramedullary fixation method has a problem in that the method fails to satisfactorily treat femoral trochanteric fractures and the like.

The present disclosure was made to solve the above problem. An object of the present disclosure is to provide a treatment tool capable of satisfactorily treating a fracture of a long tubular bone; in particular, a femoral trochanteric fracture or subtrochanteric fracture accompanied by a posterolateral defect.

Solution to Problem

The treatment tool according to the present disclosure relates to a treatment tool for use in treating fractures of long tubular bones, such as humerus, radius, ulna, femur, tibia, and fibula; for example, femoral trochanteric fractures or subtrochanteric fractures, proximal humerus fractures, and long tubular bone diaphysis fractures. The treatment tool is characterized in that the instrument comprises an elastic plate that has a curved shape or can be curved and that has at least one pressing portion that presses a fractured portion from one side by a restoring force generated by deformation of widening the curvature.

In the treatment tool according to a first preferred embodiment of the present disclosure, said pressing portion is provided on one end side in a width direction of the plate.

In the treatment tool according to the first preferred embodiment of the present disclosure, the plate comprises multiple pressing portions as the at least one pressing portion, and the pressing portions are provided at the tips of corresponding arms that are provided at intervals in a vertical direction of the plate.

In the treatment tool according to the first embodiment, the plate preferably comprises at least one second pressing portion that is provided on the other end side in the width direction of the plate so as to press the fractured portion from the other side by a restoring force that is generated by deformation of widening the curvature and thereby hold the fractured portion with said pressing portion.

In the treatment tool according to the first embodiment, said pressing portion and the second pressing portion preferably comprise an inwardly projecting hook at the tips thereof.

In the treatment tool according to the first embodiment, the hook of said pressing portion is preferably bent inwardly more than 90°.

In the treatment tool according to the first embodiment, the hook of the second pressing portion is preferably bent inwardly more than 90°.

In the treatment tool according to the first embodiment, the plate is preferably vertically symmetrical with respect to a central axis parallel to the width direction.

In the treatment tool according to a second preferred embodiment of the present disclosure, the plate has a longitudinal shape, and comprises at least one through-hole formed in an area other than said pressing portion.

In the treatment tool according to the second embodiment, the plate preferably comprises multiple through-holes formed at intervals over the entire area.

In the treatment tool according to the second embodiment, said pressing portion is preferably thicker than at least a portion of the rest of the plate.

In the treatment tool according to the second embodiment, said pressing portion is preferably one end portion of the plate that is folded back in the longitudinal direction.

In the treatment tool according to the second embodiment, the upper-end edge of the plate is preferably slanted downwardly from said pressing portion toward the other end portion in the longitudinal direction.

Preferably, the treatment tool according to the present disclosure described above is used to treat a femoral trochanteric fracture or subtrochanteric fracture; and said pressing portion preferably presses the femoral trochanter from the posterior side by a restoring force that is generated by deformation of widening the curvature. More preferably, the second pressing portion presses the femoral trochanter from the anterior side by a restoring force that is generated by deformation of widening the curvature.

Advantageous Effects

According to the treatment tool of the present disclosure, even if a posterolateral defect, which is a separation of the posterolateral portion of the trochanter from the main bone along a fracture line, occurs, for example, in a femoral trochanteric fracture or subtrochanteric fracture, said pressing portion of the plate presses a posterolateral bone fragment of the trochanter from the posterior side, whereby the lateral portion of the trochanter becomes one mass. Since the posterolateral bone fragment separated in the trochanter can be stably fixed to the main bone in this way, dehiscence of the posterolateral bone fragment from the main bone during an intramedullary nail surgery or the like in osteosynthesis can be suppressed. Further, the treatment tool can reduce the risk of complications, such as rotation of proximal femoral fragments, including the bone head, which is associated with a posterolateral defect that may occur during bone fusion after osteosynthesis, and cutout associated with displacement; therefore, femoral trochanteric fractures and the like can be satisfactorily treated. Furthermore, since the restored position of the posterolateral defect can be satisfactorily maintained, bone fusion of the posterolateral bone fragment to the main bone is not hindered until the defective posterolateral bone fragment is joined to the main bone.

In long tubular bone fractures, as well as in femoral trochanteric fractures or subtrochanteric fractures, the treatment tool of the present disclosure can stably fix separated bone fragments to each other.

DETAILED DESCRIPTION OF THE EMBODIMENTS

Embodiments of the present disclosure will be described below with reference to the accompanying drawings. The treatment tool of the present disclosure is a treatment tool for use in treating fractures of long tubular bones, such as humerus, radius, ulna, femur, tibia, and fibula; for example, femoral trochanteric fractures or subtrochanteric fractures, proximal humerus fractures, and long tubular bone diaphysis fractures. More specifically, the treatment tool according to the present disclosure is capable of satisfactorily treating a fracture by being used as an implant or a surgical instrument in the surgical operation of a fracture (osteosynthesis). For example, in the surgical operation (osteosynthesis) for a femoral trochanteric fracture or subtrochanteric fracture, the treatment tool can be used as an implant together with an existing instrument, such as an intramedullary nail or a compression hip screw; or used as a surgical instrument required in a surgery with an intramedullary nail or the like, thereby satisfactorily treating a femoral trochanteric fracture or the like.

In the following embodiment, explanation is made using, as an example, the case in which the treatment tool according to the present disclosure is applied to treat a femoral trochanteric fracture.

Figure 1:
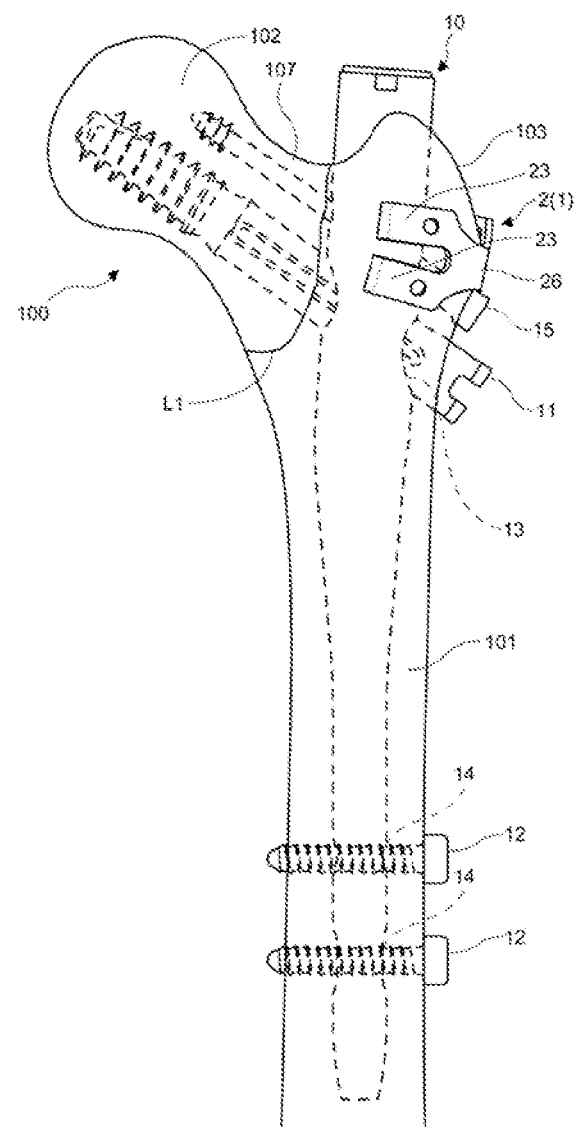
FIG. 1 is a front view showing a state in which the treatment tool according to the first embodiment is attached to the left femur.
Figure 2:
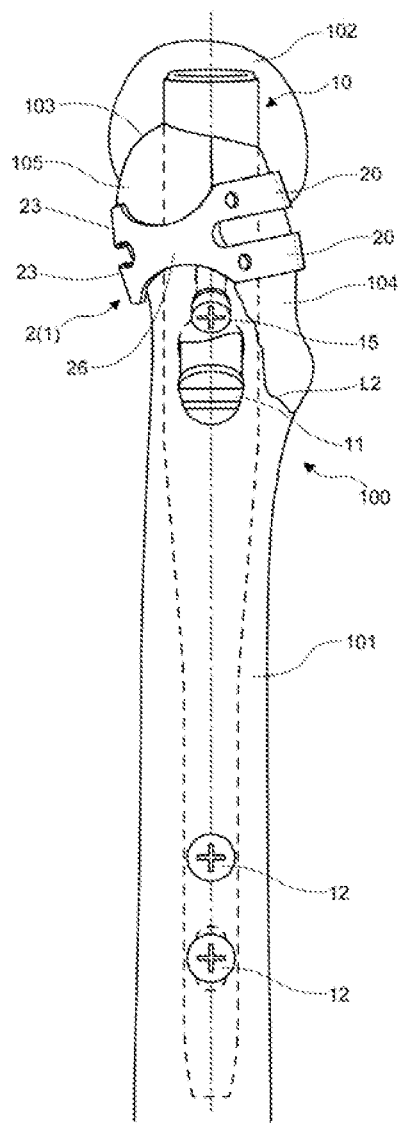
FIG. 2 is a side view showing a state in which the treatment tool according to the first embodiment is attached to the left femur.
Figure 3:
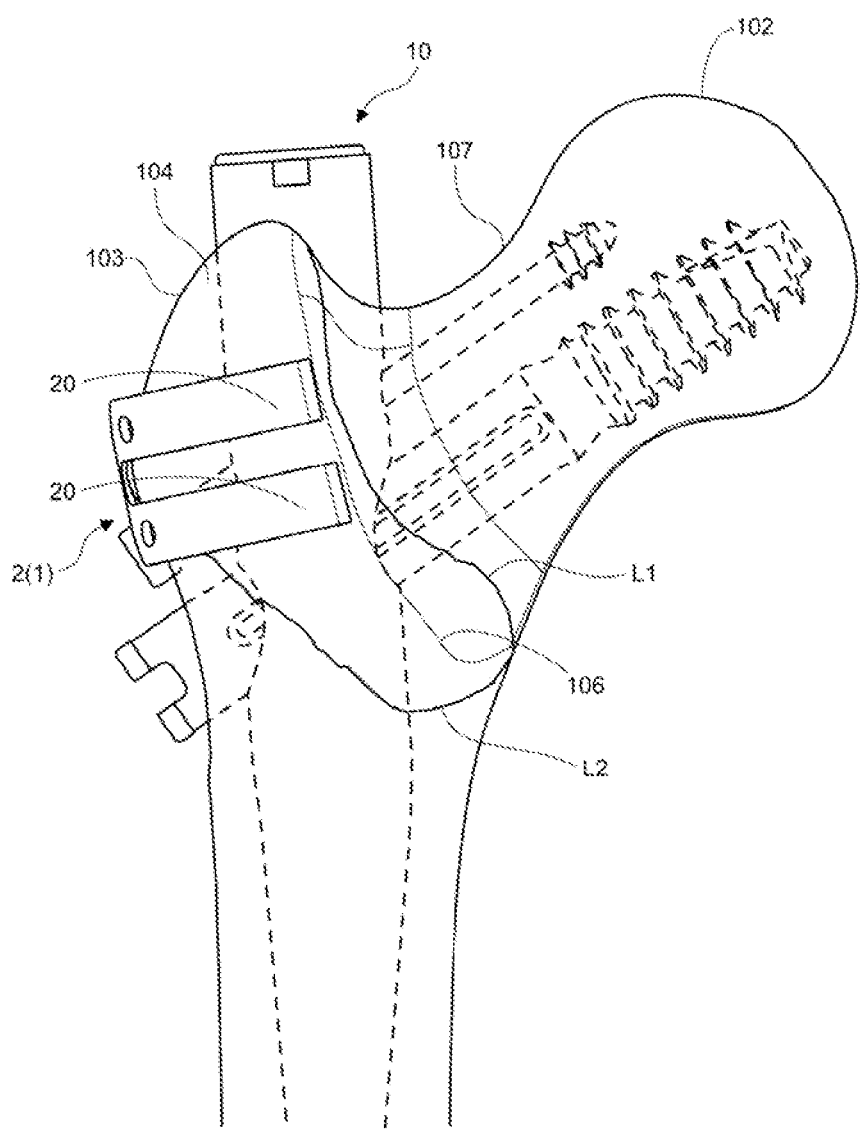
FIG. 3 is a rear view showing a state in which the treatment tool according to the first embodiment is attached to the left femur.
Figure 4:
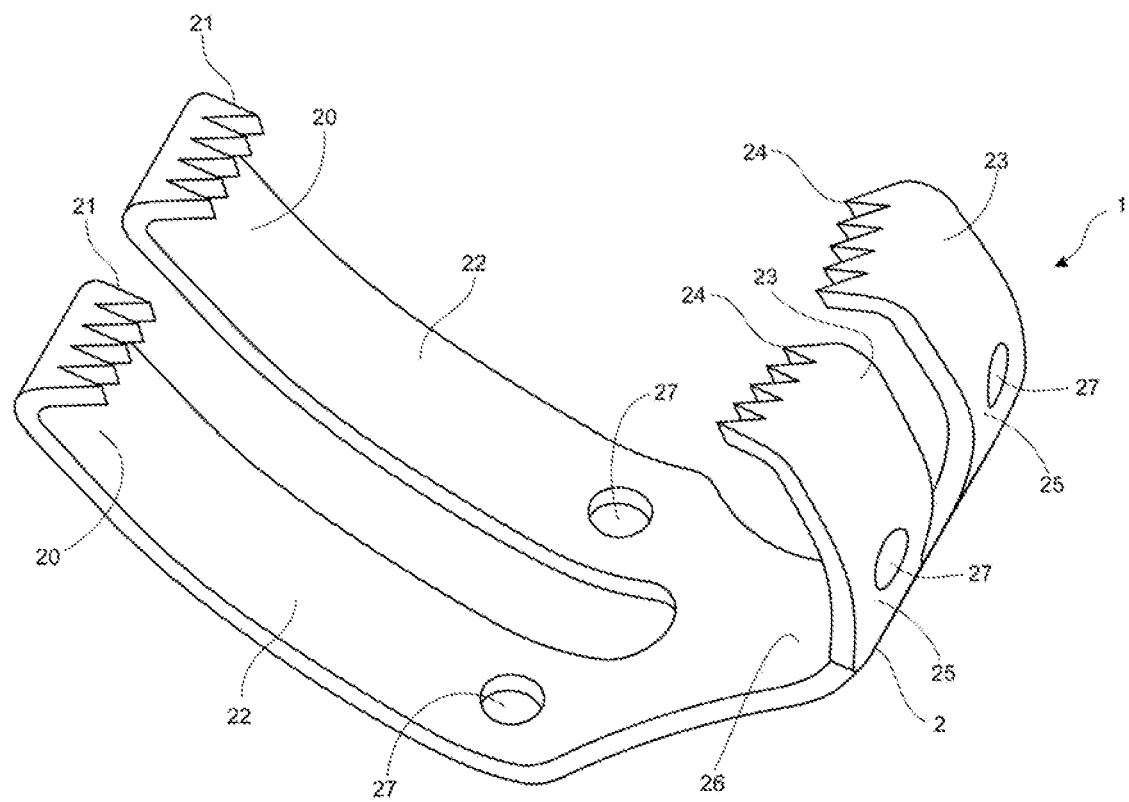
FIG. 4 is a perspective view of the treatment tool according to the first embodiment.
Figure 5:
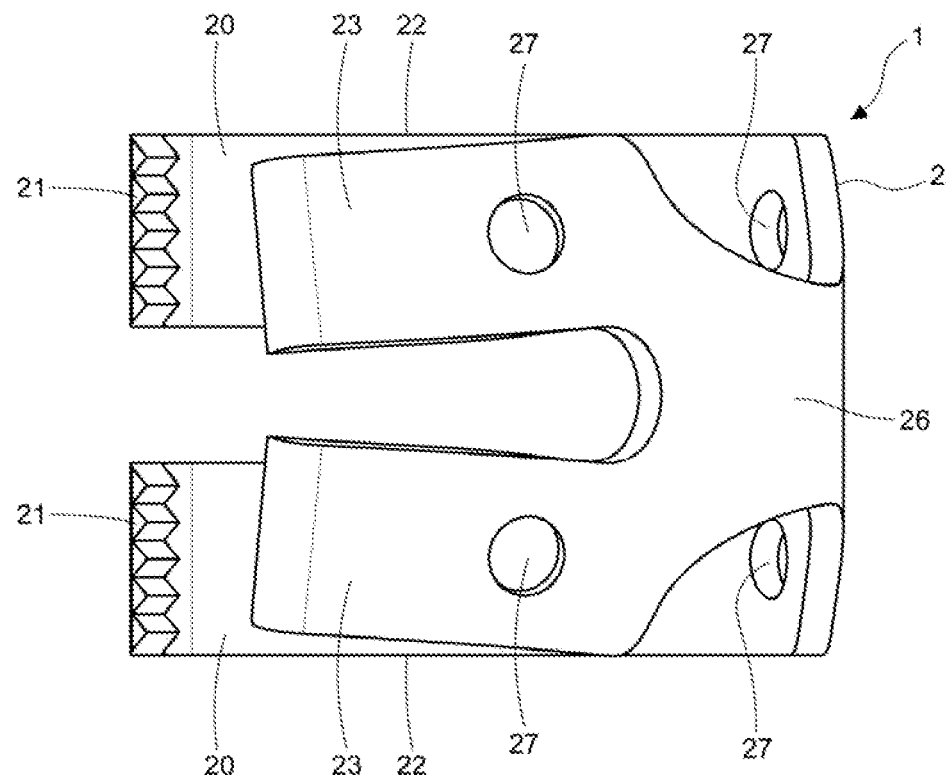
FIG. 5 is a front view of the treatment tool according to the first embodiment.
Figure 6:
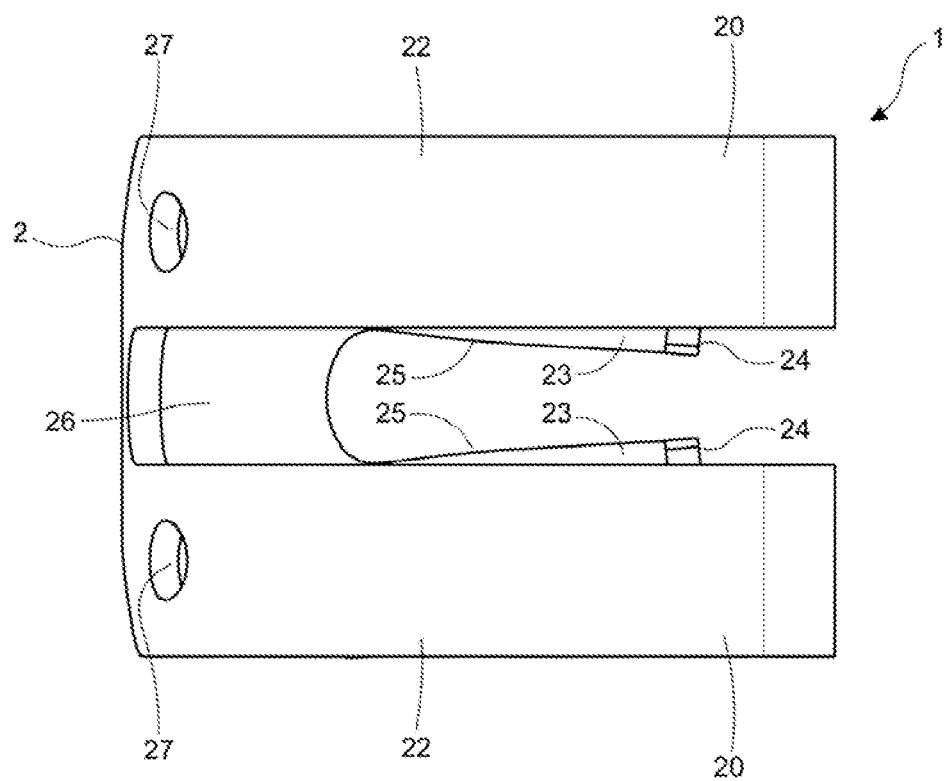
FIG. 6 is a rear view of the treatment tool of the first embodiment.
Figure 7:
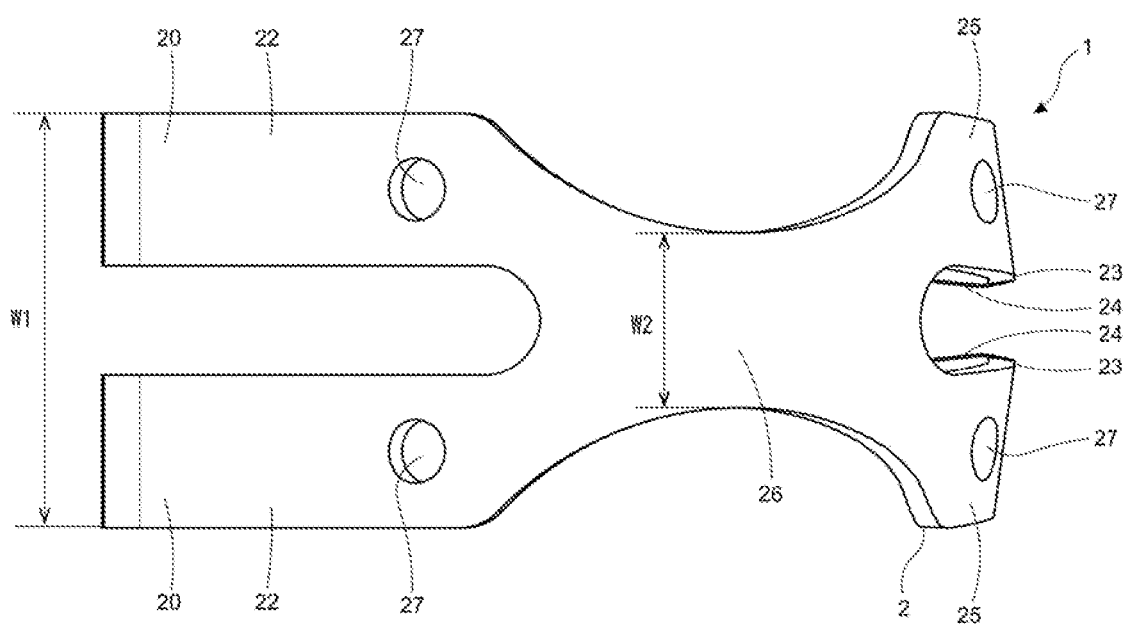
FIG. 7 is a right-side view of the treatment tool according to the first embodiment.
Figure 8:
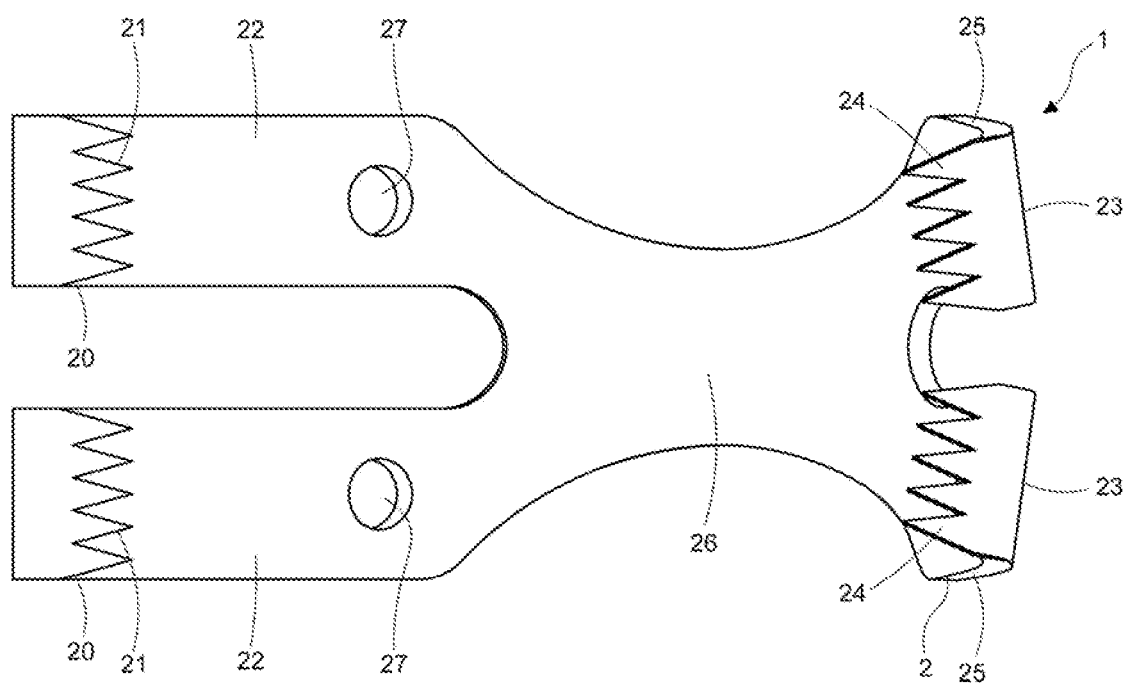
FIG. 8 is a left-side view of the treatment tool according to the first embodiment.
Figure 9:
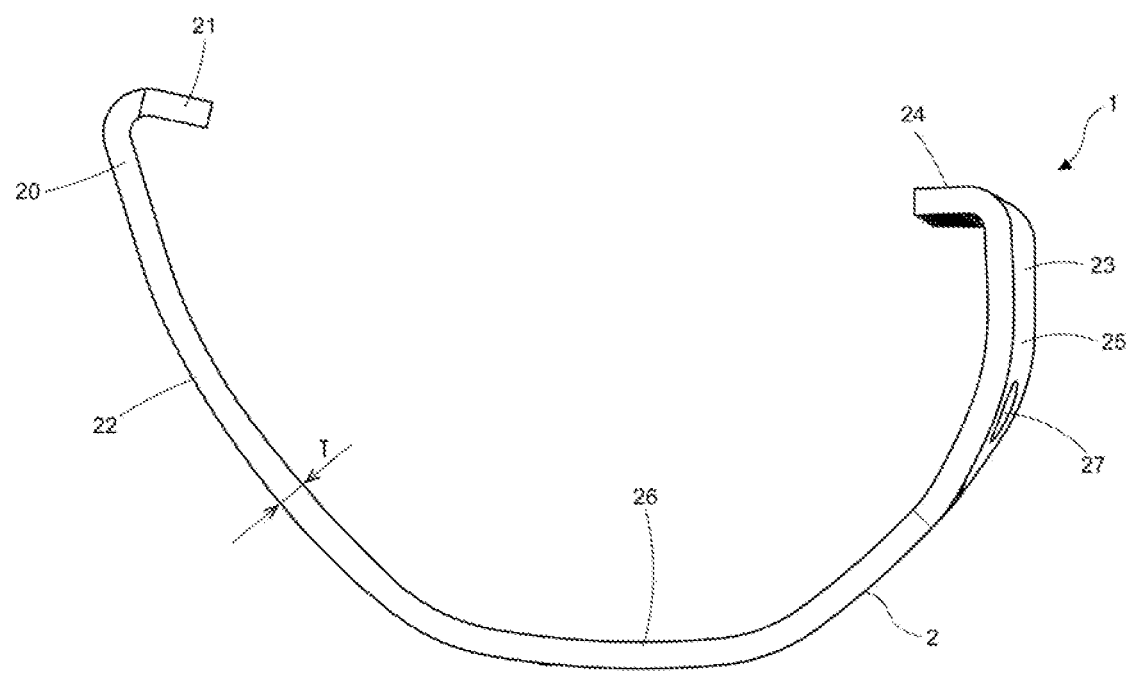
FIG. 9 is a plan view of the treatment tool according to the first embodiment.

FIGS. 1 to 3 show a state in which an intramedullary nail 10 and the treatment tool 1 are attached to treat, for example, a trochanteric fracture (shown as fracture line L1 in FIG. 1 etc.) of the femur 100 (left femur in the illustrated example). In the present disclosure, the upper side of FIGS. 1 to 3 is the proximal side, and the lower side is the distal side. The left side of FIG. 1 is the medial side, and the right side of FIG. 1 is the lateral side. The left side of FIG. 2 is the forward side, and the right side of FIG. 2 is the backward side. Similarly, in FIG. 10, the upper side is the proximal side, the lower side is the distal side, the back side is the medial side, the front side is the lateral side, the left side is the forward side, and the right side is the backward side.

The intramedullary nail 10 is inserted into the intramedullary cavity of the femur 100 from above. The intramedullary nail 10 comprises a connector 11 and a fixing bolt 12 for fixing the intramedullary nail 10 to the diaphysis 101. The connector 11 is inserted diagonally upward from the lateral surface of the diaphysis 101 toward the bone head 102. The intramedullary nail 10 is formed of a biocompatible material, such as titanium, titanium alloy, or stainless steel.

The intramedullary nail 10 has an insertion hole 13 formed on the proximal side into which a connector 11 is inserted. The insertion hole 13 penetrates the intramedullary nail 10 so as to extend obliquely upward. The connector 11 is inserted obliquely upward toward the bone head 102 through the insertion hole 13. The intramedullary nail 10 has one or more (two in the present embodiment) through-holes 14 formed on the distal side through which the fixing bolts 12 are inserted. The through-holes 14 penetrate the intramedullary nail 10 so as to extend substantially horizontally; accordingly, when the fixing bolts 12 are screwed horizontally toward the diaphysis 101, bone fragments, including the bone head 102, separated by the fracture, are captured by a screw provided in the tip portion of the fixing bolts, and thereby fixed.

In FIGS. 1 and 2, reference numeral 15 indicates an auxiliary connector that penetrates the intramedullary nail 10 and is inserted diagonally upward toward the bone head 102, so as to extend in parallel with the connector 11. A screw is also formed at the tip of the auxiliary connector 15. Bone fragments are also captured by the screw of the auxiliary connector 15, and thereby fixed by the auxiliary connector 15. Capturing the bone fragments in this manner by the auxiliary connector 15 as well as by the connector 11 can prevent rotation of bone fragments (bone head 102) during treatment. The intramedullary nail 10 is not necessarily configured to include the auxiliary connector 15.

In the treatment of a femoral trochanteric fracture with an intramedullary nail 10, if a fracture occurs on the lateral surface of the trochanter 103 as shown by the fracture line L2 in FIG. 2 and is accompanied by a posterolateral defect, which is a separation of the posterolateral portion of the trochanter 103 from the main bone 105, the intramedullary nail 10 fails to fix to the main bone 105 a posterolateral bone fragment 104 separated due to this defect; therefore, the femoral trochanteric fracture is treated in an unstable state such that the posterolateral bone fragment 104 is not fixed to the main bone 105. However, this unstable state, in which the posterolateral bone fragment 104 is not fixed to the main bone 105, causes complications such as rotation of the bone head 102, prolonged fusion, and cutout during the treatment of the femoral trochanteric fracture. This hinders osteosynthesis of the femoral trochanteric fracture, and the femoral trochanteric fracture thus cannot be treated satisfactorily.

Accordingly, when a femoral trochanteric fracture is accompanied by a posterolateral defect, the treatment tool 1 according to this embodiment enables a posterolateral bone fragment 104, which is separated due to a defect of the trochanter 103, to be fixed to the main bone 105. This reduces the risk of complications, such as rotation of the bone head 102, prolonged fusion, and cutout during bone fusion of femoral trochanteric fracture; and can also maintain the restored position of the defective posterolateral bone fragment 104. In addition, in the surgery with an intramedullary nail 10 or the like, a posterolateral bone fragment 104, which has been separated due to a defect, can be fixed to the main bone 105; accordingly, the restored position of the posterolateral bone fragment 104 can be maintained during the period from before implantation of the intramedullary nail 10 to completion of the implantation.

FIGS. 4 to 9 show the appearance of the treatment tool 1 according to the first embodiment. The treatment tool 1 comprises a plate 2 having a predetermined thickness. The plate 2 is elastic and has a curved shape formed by bending the plate 2 so as to curve along the width direction in plan view. This curved shape not only refers to an arc shape and a smooth curved shape, but also includes a shape formed by bending so as to surround a part of the femur. Examples of materials for the plate 2 include materials having biocompatibility, such as titanium, titanium alloy, and stainless steel. The plate 2 has a longitudinal shape. The longitudinal shape means a shape in which the length in the horizontal direction (width direction) is sufficiently longer than the length in the vertical direction (height direction) perpendicular to the horizontal direction (width direction). In the following description, the width direction of the plate 2 is referred to as the longitudinal direction. In the first embodiment, the plate 2 has a longitudinal shape. However, the plate 2 does not necessarily require a longitudinal shape. The plate 2 may have a roughly square shape of approximately the same length in the horizontal direction (width direction) and the vertical direction (height direction).

The plate 2 is placed above the connector 11 and the auxiliary connector 15 of the intramedullary nail 10 relative to the femur 100. The plate 2 has a length that extends from the back of the trochanter 103 of the femur 100 toward the front of the trochanter 103 by passing around the greater trochanter; i.e., a length such that both end portions of the plate in the longitudinal direction straddle the great trochanter of the femur 100, and extend to the anterior and posterior surfaces of the trochanter 103.

The degree of curvature of the curved shape of the plate 2 is set higher than that of the surface configuration from the back of the trochanter 103 of femur 100 to the front of the trochanter 103 through the greater trochanter. When the plate 2 is installed on the femur 100, both ends of the plate 2 are opened so as to widen the curvature of the plate 2. This allows the plate 2 to be wound around the trochanter 103 by a restoring force that is generated by deformation of widening the curvature of the plate 2; accordingly, the plate 2 can be attached to the trochanter 103 without using any fixing means, such as screws. Furthermore, the trochanter 103 of the femur 100 is held from both the anterior and posterior sides by the two end portions of the plate 2, and a posterolateral bone fragment 104, which is one of the two bone fragments separated due to a defect of the trochanter 103, is pressed against the main bone 105, which is the other of the two bone fragments; therefore, the separated posterolateral bone fragment 104 can be fixed to the main bone 105. The restoring force generated by deformation of the plate 2 described above may be a restoring force generated by elastic deformation, or may be a restoring force generated by spring-back (elastic recovery) during plastic deformation.

The degree of curvature of the curved shape of the plate 2 is basically set higher than that of the surface configuration of the trochanter 103 as described above. However, the degree of curvature is not particularly limited. If the fixing force with which the plate 2 is attached to the femur 100 is weak, the surgeon can bend the plate 2 to adjust the degree of curvature, and then re-install the plate 2.

At least one pressing portion 20 that abuts on the posterior surface of the trochanter 103 of the femur 100 is provided at one end side in the longitudinal direction of the plate 2. In this embodiment, the plate 2 comprises two pressing portions 20. The two pressing portions 20 are provided at the tips of two arms 22. The two arms 22, which are spaced apart from each other in the vertical direction of the plate 2 and extend in parallel, are provided at one end side of the plate 2 by forming a notch extending longitudinally at the center position in the vertical direction of the plate 2. The pressing portions 20 press one of the at least two bone fragments separated by fracture against the other bone fragment.

The length of the plate 2 is preferably set so that when the center of the substantially central portion 26 in the longitudinal direction is positioned approximately at the bony protrusion outside of the greater trochanter of the femur 100, the pressing portion 20 is in contact with the posterior surface of the trochanter 103 in the vicinity of the intertrochanteric crest 106. The vicinity of the intertrochanteric crest 106 means that the contact position of the pressing portion 20 is not only a position immediately above the intertrochanteric crest 106, but also may be a position in the lateral region before reaching the intertrochanteric crest 106 or a position in the medial region that goes beyond the intertrochanteric crest 106. When the pressing portion 20 is in contact with a lateral position before reaching the intertrochanteric crest 106, the hook 21 described below can prevent the pressing portion 20 from coming in contact with the blood vessel inside the intertrochanteric crest 106. The lateral position before reaching the intertrochanteric crest 106 refers to a position within the range of 15 mm or less from the intertrochanteric crest 106. When the pressing portion 20 is in contact with a position immediately above the intertrochanteric crest 106 or a position in the medial region that goes beyond the intertrochanteric crest 106, it is preferably set so that the pressing portion 20 (including the hook 21 described below) does not come into contact with the blood vessel inside the intertrochanteric crest 106. The intertrochanteric crest 106 refers to a protruding portion between the trochanter 103 and the neck 107 on the posterior surface side of the femur 100.

The pressing portion 20 has an inwardly projecting hook 21 at the tip. The hook 21 can increase the pressing force that presses the trochanter 103 (or the soft tissue on the trochanter 103) on the posterior side of the femur 100; accordingly, the posterolateral bone fragment 104 separated due to a defect of the trochanter 103 can be firmly fixed to the main bone 105.

In this embodiment, the hook 21 is formed by bending the tip of the pressing portion 20 inwardly. The tip edge of the hook 21 constitutes an acutely pointed blade edge. The blade edge may have a jagged shape, such as a saw-blade shape; or may have a straight extending shape. The angle at which the hook 21 of the pressing portion 20 bends inwardly is not particularly limited. The hook 21 is preferably bent inwardly at more than 90°. This allows the hook 21 of the pressing portion 20 to be sharply engaged with the posterolateral bone fragment 104; accordingly, the plate 2 can be stably attached to the trochanter 103 (posterolateral bone fragment 104) by the hook 21.

At least one second pressing portion 23 that abuts on the anterior surface of the trochanter 103 of the femur 100 is provided on the other end side of the plate 2. In this embodiment, the plate 2 comprises two second pressing portions 23. The two second pressing portions 23 are provided at the tips of two arms 25. The two arms 25, which are spaced apart from each other in the vertical direction of the plate 2 and extend in parallel, are provided on the other end side of the plate 2 in the longitudinal direction by forming a notch extending longitudinally at the center position in the vertical direction of the plate 2. The second pressing portions 23 hold at least two bone fragments separated by a fracture with the pressing portions 20.

As long as the second pressing portion 23 holds the trochanter 103 with the pressing portions 20 when the plate 2 is installed on the trochanter 103 of the femur 100, the contact position of the second pressing portion 23 with the anterior surface of the trochanter 103 is not particularly limited. The contact position may be the opposing position facing the pressing portion 20 across the trochanter 103, or may be a position in the lateral region before reaching the opposing position, or a position in the medial position that goes beyond the opposing position.

The second pressing portion 23 has an inwardly projecting hook 24 at the tip. The hook 24 can increase the pressing force that presses the trochanter 103 (or the soft tissue on the trochanter 103) on the anterior side of the femur 100, so that the posterolateral bone fragment 104 separated due to a defect of the trochanter 103 can be securely fixed to the main bone 105.

In this embodiment, the hook 24 is formed by bending the tip of the pressing portion 20 inwardly, similar to the hook 21. The tip edge of the hook 24 constitutes an acutely pointed blade edge. The blade edge may have a jagged shape, such as a saw-blade shape, or may have a straight extending shape. The angle at which the hook 24 of the pressing portion 23 bends inwardly is not particularly limited. The hook 24 is preferably bent inwardly at 90°. This allows the hook 24 of the second pressing portion 23 to be securely and sharply engaged with the main bone 105; accordingly, the plate 2 can be stably attached to the trochanter 103 (the main bone 105) by the hook 24.

The plate 2 is formed in such a manner that the upper-end edge and the lower end edge of the substantially central portion 26 are curved in a concave shape, and the substantially central portion 26 is constricted. Minimizing excess portions at the upper and lower end edges of the plate 2 in this way can suppress the interference of the plate 2 with body tissues when the plate 2 is fixed to the trochanter 103 of the femur 100. Therefore, the pain and discomfort the patient feels can be reduced when the treatment tool 1 is attached. Further, it is possible to prevent the interference of the plate 2 with the connector 11 and the auxiliary connector 15.

The length (longitudinal size) of plate 2 is not particularly limited, as long as the plate 2 can extend from the back of the trochanter 103 of femur 100 to the front of the trochanter 103 by passing around the greater trochanter. The length of the plate in an expanded state (excluding the lengths of the hooks 21 and 24) is, for example, in the range of 30 mm or more and 90 mm or less, more preferably 40 mm or more and 80 mm or less, and more preferably 50 mm or more and 70 mm or less. When the length is set within the above-mentioned range, even if there is a difference in physique among a large number of people, in particular, elderly people who are prone to femoral fractures, the pressing portion 20 and the second pressing portion 103 can be appropriately brought into contact with the aforementioned contact positions of the trochanter 103.

The length of the hooks 21, 24 is not particularly limited. For example, the length is set within the range of 1 mm or more and 10 mm or less, and more preferably 3 mm or more and 7 mm or less.

The height (size in the vertical direction) W1 of the plate 2 is not particularly limited. For example, the height W1 is set within the range of 10 mm or more and 30 mm or less, and more preferably 16 mm or more and 24 mm or less. The height W2 of the substantially central portion 26 of the plate 2 is also not particularly limited. For example, the height W2 is set within the range of 2 mm or more and 20 mm or less, and more preferably 4 mm or more and 12 mm or less.

The thickness T of the plate 2 is not particularly limited, and is appropriately set according to the material selected as a material for the plate 2. For example, the thickness of the plate 2 is set within the range of 0.5 mm or more and 3.0 mm or less, more preferably 0.8 mm or more and 2.0 mm or less, and more preferably 1.0 mm or more and 1.5 mm or less.

Through-holes 27, which correspond to the pressing portions 20 and the second pressing portions 23, are provided on one end side and the other end side from the substantially central portion 26 in the longitudinal direction of the plate 2. The through-holes 27 are holes for hooking surgical instruments when the plate 2 is attached to or detached from the femur 100. It is also possible to pass screws through the through-holes 27 when the plate 2 must be screwed to the trochanter 103 of the femur 100. The through-holes 27 do not necessarily have to be formed in the plate 2.

The plate 2 is formed so as to be vertically symmetrical with respect to the central axis parallel to the longitudinal direction. Thus, one type of treatment tool 1 is applicable to both the left and right femurs, without distinction between left and right. The plate 2 does not necessarily have to be formed to be vertically symmetrical with respect to the central axis.

Next, the procedure of the surgical operation (osteosynthesis) of a femoral trochanteric fracture using the treatment tool 1 according to the first embodiment is briefly described. First, the plate 2 is inserted into the body through an incision in the vicinity of the lateral surface of the trochanter 103 using forceps or by hand, and then the second pressing portion 23 on the anterior side is brought into contact with the anterior surface of the trochanter 103 at an appropriate position to engage the hook 24 with the main bone 105. Then, while widening the plate 2, the pressing portion 20 on the posterior side is positioned in the vicinity of the intertrochanteric crest 106 on the posterior surface of the trochanter 103, and the hook 21 is engaged with a posterolateral bone fragment 104 separated due to a defect of the trochanter 103 by a restoring force that is generated by deformation of widening the plate 2; accordingly, the plate 2 is wound around the trochanter 103, and fixed to the trochanter 103. The plate 2 may be widened by opening the pressing portion 20 using an appropriate instrument, or may be naturally widened by pressing the pressing portion 20 deeply so as to open the pressing portion 20 in conformity with the surface shape of the trochanter 103.

Next, an intramedullary nail 10 is attached to a conventionally known insertion device (not shown). The skin above the trochanter 103 of the femur 100 is then incised, and a perforation is formed in the femur 100 with a drill (not shown). The intramedullary nail 10 is inserted into the medullary cavity using an instrument for insertion. The skin in the vicinity of the lateral surface of the trochanter 103 is then incised, and a connector 11 and an auxiliary connector 15 are inserted toward the bone head 102 and supported by the intramedullary nail 10 inserted into the medullary cavity, whereby bone fragments including the bone head 102 separated by a fracture are connected to the trochanter 103. The skin in the vicinity of the lateral surface of the diaphysis 101 is then incised; and a fixing bolt 12 is screwed into the diaphysis 101 through a through-hole 14 of the intramedullary nail 10, thereby fixing the intramedullary nail 10 to the diaphysis 101.

According to the treatment tool 1 of the first embodiment, when the plate 2 is installed on the trochanter 103 of the femur 100, a restoring force generated by deformation of widening the plate 2 presses a posterolateral bone fragment 104 against the main bone 105; accordingly, when the posterolateral bone fragment 104 is separated from the main bone 105 due to a defect of the trochanter 103, a surgery with an intramedullary nail 10 during osteosynthesis and bone fusion after osteosynthesis can be performed in a stable state such that the posterolateral bone fragment 104 is fixed to the main bone 105. In other words, in the surgery with an intramedullary nail 10 that has been performed until now, after a posterolateral bone fragment 104 was temporarily fixed to the main bone 105 with forceps or the like, the intramedullary nail 10 was inserted and the forceps were then removed. However, after the forceps were removed, the restored position of the defective posterolateral bone fragment 104 was not maintained; this led to complications such as bone head rotation and prolonged fusion during the subsequent bone fusion. In contrast, when the treatment tool 1 according to the first embodiment is used, the risk of complications such as bone head rotation and prolonged fusion associated with a posterolateral defect can be reduced during bone fusion; accordingly, a femoral trochanteric fracture can be satisfactorily treated and the defective posterolateral bone fragment 104 can be fixed to the main bone 105 without separation from each other until the posterolateral bone fragment 104 is joined to the main bone 105, whereby the fusion of these two is not hindered and the restored position can be satisfactorily maintained. Further, in the surgery with an intramedullary nail 10, a defective posterolateral bone fragment 104 can be fixed to the main bone 105, and the posterolateral bone fragment 104 can be maintained in the restored position during the period from before implantation of the intramedullary nail 10 to completion of the implantation; therefore, there is no need to use forceps for temporary fixation. Unlike forceps, the treatment tool 1 of the first embodiment has no handle, and therefore does not interfere with the surgical field during the surgery with the intramedullary nail 10; and can also reduce the size of skin to be incised to insert the treatment tool 1 into the body.

According to the treatment tool 1 of the first embodiment, the plate 2 comprises second pressing portions 23. Since the pressing sections 20 and the second pressing sections 23 hold the trochanter 103 from both the anterior and posterior sides and the plate 2 is wound around the trochanter 103 by a restoring force generated by deformation of widening the plate 2, the treatment tool 1 can be attached to the femur 100 without using any fixing means. This can reduce the degree of invasion of the body, thus reducing burden on the patient.

Further, according to the treatment tool 1 of the first embodiment, arms 22 and arms 25 are formed by bifurcation from a substantially central portion 26 of the plate 2; and pressing portions 20 and second pressing portions 23 are provided at the tips of the arms 22 and arms 25, respectively. The bone surface is three-dimensional, has undulations, and varies in height. Accordingly, bifurcation of the arms 22 and 25 makes it easier for the pressing portions 20 and 23 to be in contact with the bone surface along the undulations on the bone surface, whereby the pressing portions 20 and 23 can effectively press the trochanter 103. In contrast, if the arms 22 and arms 25 are not bifurcated arms, parts of the pressing portions 20 and the second pressing portions 23 are in a state of floating away from the bone surface without being in contact with the bone surface; therefore, the pressing force with which the pressing portions 20 and pressing portions 23 press the trochanter 103 may be attenuated. The arms 22 and arms 25 may be formed by trifurcation or more from a substantially central portion 26 of the plate 2.

Furthermore, the treatment tool 1 according to the first embodiment can be independently attached to the femur 100 without interference with the intramedullary nail 10, which is an existing device for treating a femoral trochanteric fracture. Therefore, the treatment tool 1 can be attached to the position intended by the practitioner, and can also be used in combination with the existing intramedullary nail 10. Although an explanation in this regard is omitted, the treatment tool 1 can also be used in combination with a compression hip screw used for the treatment of femoral neck fractures.

The treatment tool 1 according to one embodiment of the present disclosure is described above. However, the treatment tool of the present disclosure is not limited to the above embodiment. Various modifications can be made within the spirit of the present disclosure.

For example, in the treatment tool 1 according to the first embodiment, the plate 2 has two pressing portions 20 and two second pressing portions 23. However, there is no limitation on the number of the pressing portions 20 and the second pressing portions 23. The plate 2 may have one pressing portion 20 and one second pressing portion 23, or may have three or more of each. The number of the pressing portions 20 may be different from the number of the second pressing portion 23. For example, the treatment tool 1 may have two pressing portions 20 and one second pressing portion 23.

In addition, in the treatment tool 1 according to the first embodiment, hooks 21 and hooks 24 are formed by inwardly bending the tips of the pressing portions 20 and the second pressing portions 23, respectively. However, the configuration is not limited thereto. For example, a circular, semicircular, rectangular, trapezoidal, triangular, or like-shaped protrusion in cross-sectional view may be integrally formed at the tips of the pressing portions 20 and the second pressing portions 23 to increase the force of pressing the trochanter 103 (or the soft tissue on the trochanter 103) by the pressing portions 20 and the second pressing portions 23. Each of the two end portions of the plate 2 can be folded back on itself to thereby increase the thickness of the pressing portions 20 and the second pressing portions 23, thus increasing the force of pressing the trochanter 103 by the pressing portions 20 and the second pressing portions 23 (or the soft tissue on the trochanter 103).

In addition, according to the first embodiment, if the treatment tool 1 is installed as an implant before implantation of the intramedullary nail 10 in the surgery with an intramedullary nail 10, a defective posterolateral bone fragment 104 can be fixed to the main bone 105 during the period until the implantation is completed, and the restored position can be satisfactorily maintained until bone fusion is obtained. Alternatively, however, during the period until the intramedullary nail 10 is implanted, a defective posterolateral bone fragment 104 may be temporarily fixed to the main bone 105 by forceps or the like; and after the implantation of the intramedullary nail 10 is completed and the forceps are removed, the treatment tool 1 may be used as an implant to fix the defective posterolateral bone fragment 104. Further, alternatively, in the surgery with an intramedullary nail 10, the treatment tool 1 may be used only as a surgical instrument to fix a defective posterolateral bone fragment 104 to the main bone 105 during the period until implantation of the intramedullary nail 10 is completed; and may be removed after implantation of the intramedullary nail 10 is completed.

Figure 10:
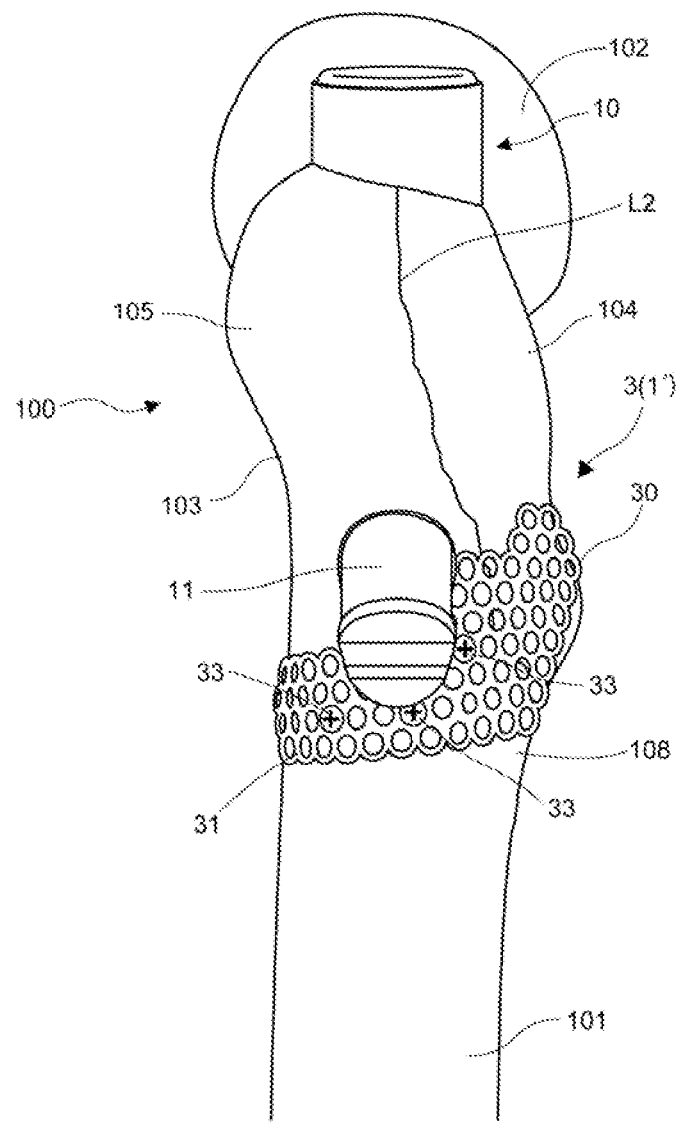
FIG. 10 is a side view showing a state in which the treatment tool according to the second embodiment is attached to the left femur.
Figure 11:
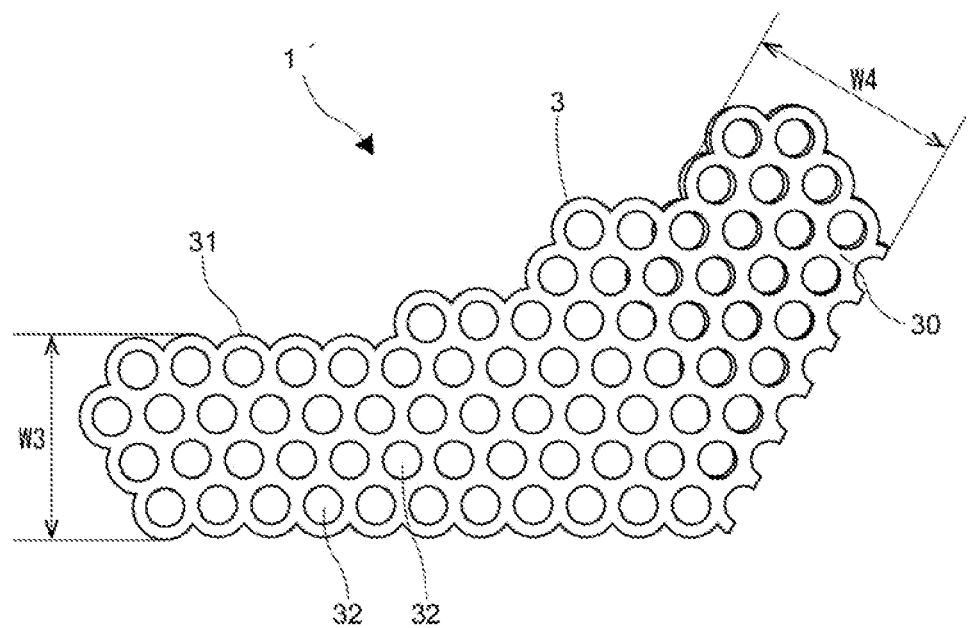
FIG. 11 is a side view showing a state before the treatment tool according to the second embodiment is curved.

FIG. 10 shows a state in which the treatment tool 1' according to a second embodiment is attached to the femur 100 (left femur in the illustrated example). FIG. 11 shows the appearance of the treatment tool 1' according to the second embodiment. The auxiliary connector 15 is omitted in FIG. 10.

The treatment tool 1' comprises a longitudinal plate 3 having a predetermined thickness. The plate 3 according to this embodiment does not extend straight in the horizontal (width) direction, but is bent diagonally upward from a midway in the horizontal (width) direction. The plate 3 is elastic, and has a curved shape formed by bending to curve along the longitudinal direction in plan view. The curved shape does not only refer to an arc shape or a smooth curved shape, but also includes a shape bent so as to surround a part of the femur. Examples of the material of the plate 3 include biocompatible materials, such as titanium, titanium alloy, and stainless steel.

The plate 3 is placed below the connector 11 of the intramedullary nail 10 relative to the femur 100. The plate 3 has a length that extends from the posterior surface of the trochanter 103 of the femur 100 to reach the lateral surface; i.e., a length such that when one end portion in the longitudinal direction is allocated to the lateral portion of the lower trochanter 108 below the trochanter 103 of the femur 100, the other end portion reaches the posterior surface of the trochanter 103.

The height (size in the vertical direction) W3, W4 of the plate 3 is not particularly limited. For example, the height can be set within the range of 3 mm or more and 20 mm or less, more preferably 9 mm or more and 16 mm or less. The thickness of the plate 3 is not particularly limited, and can be appropriately set according to the material selected as a material for the plate 3. The thickness can be set, for example, within a range of 0.3 mm or more and 3 mm or less, more preferably within a range of 0.3 mm or more and 2 mm or less, and even more preferably within a range of 0.3 mm or more and 1 mm or less.

The degree of curvature of the curved shape of the plate 3 is set higher than that of the surface configuration that extends from the back of the trochanter 103 of femur 100 to the lateral portion of the lower trochanter 108 by passing around the greater trochanter. When the plate 3 is installed on the femur 100, both ends of the plate 2 are opened so as to widen the curvature of the plate 3. This allows one end portion of the plate 3 to support the trochanter 103 of the femur 100 from the posterior side by a restoring force that is generated by deformation of widening the curvature of the plate 3; accordingly, a posterolateral bone fragment 104 separated due to a defect of the trochanter 103 is pressed against the main bone 105, whereby the separated posterolateral bone fragment 104 can be fixed to the main bone 105.

The degree of curvature of the curved shape of the plate 3 is basically set higher than that of the surface configuration from the back of the trochanter 103 of the femur 100 to the lateral portion of the lower trochanter 108 as described above. However, the degree of curvature is not particularly limited. If the fixing force with which the plate 3 is attached to the femur 100 is weak, the surgeon can bend the plate 3 to adjust the degree of curvature, and then re-install the plate 3.

Figure 12:
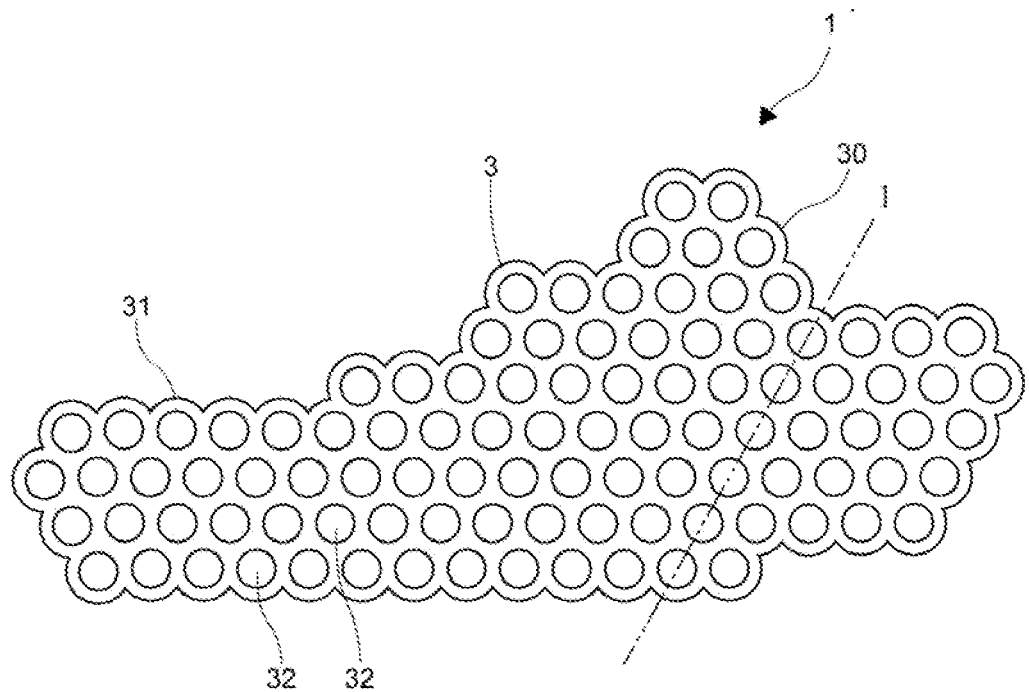
FIG. 12 is a side view showing a state before an end portion of the treatment tool according to the second embodiment is folded back.

A pressing portion 30 that abuts on the posterior surface of the trochanter 103 of the femur 100 is provided at one end side in the longitudinal direction of the plate 3. A fixing portion 31 to be fixed to the main bone 105 of the femur 100 is provided at the other end side in the longitudinal direction of the plate 3. As shown in FIG. 12, the pressing portion 30 is provided at one end in the longitudinal direction of the plate 3 by folding back one end portion of the plate 3 in the longitudinal direction along a predetermined bending line 1 so as to be overlaid on the plate 3. This overlaid portion of the plate 3 has a symmetrical shape with respect to the bending line 1. Folding back one end portion of the plate 3 in the longitudinal direction to form a pressing portion 30 in this way can increase the thickness of the pressing portion 30 to thereby increase the force of pressing a posterolateral bone fragment 104 against the main bone 105 by the pressing portion 30. The pressing portion 30 does not necessarily have to be formed by folding back one end portion of the plate 3 in the longitudinal direction at the folding line 1 described above, but may be formed by folding back one end portion of the plate 3 in the longitudinal direction at a folding line at any other position.

The length of the plate 3 is preferably set so that when the pressing portion 30 is in contact with the posterior surface of the trochanter 103 in the vicinity of the intertrochanteric crest 106, the fixing portion 31 at the other end side in the longitudinal direction is brought into contact with the main bone 105 of the femur 100 while obtaining a restoring force. The vicinity of the intertrochanteric crest 106 means that the contact position of the pressing portion 30 is not only a position immediately above the intertrochanteric crest 106, but also a position in the lateral region before reaching the intertrochanteric crest 106 or a position in the medial region that goes beyond the intertrochanteric crest 106. When the pressing portion 30 is in contact with the lateral position before reaching the intertrochanteric crest 106, the pressing portion 30 can be prevented from being in contact with the blood vessel inside the intertrochanteric crest 106. The lateral position before reaching the intertrochanteric crest 106 refers to a position within a range of 15 mm or less from the intertrochanteric crest 106. When the pressing portion 30 is in contact at a position immediately above the intertrochanteric crest 106 or a position in the medial region that goes beyond the intertrochanteric crest 106, it is preferably set so that the pressing portion 30 does not come into contact with the blood vessel inside the intertrochanteric crest 106.

The plate 3 is configured so that the upper edge is slanted downward from the pressing portion 30 toward the fixing portion 31. This allows the fixing portion 31 at the other end side in the longitudinal direction to be disposed to cover the lateral portion of the lower trochanter 108 of the femur 100 when the plate 3 is installed on the femur 100. This configuration prevents interference of the plate 3 with the connector 11 even when the connector 11, which is disposed immediately above the plate 3, protrudes from the lateral surface of the diaphysis 101. The mode of slant of the upper-end edge of the plate 3 from the pressing portion 30 toward the fixing portion 31 may be curved, linear, or a combination thereof. Any mode of slant is acceptable.

The plate 3 has at least one through-hole 32 in the fixing portion 31. This through-hole 32 can serve as a hole through which a screw 33 can be passed to fix the plate 3 to the femur 100 by screw-fastening. In this embodiment, multiple through-holes 32 are formed uniformly at intervals over the entire area of the plate 3. This allows for appropriate screwing at any site, and also makes it easier to follow the surface configuration of the femur 100 because the plate 3 can be easily curved in its entirety. The through-holes 32 do not necessarily have to be formed over the entire area of the plate 3. While multiple through-holes 32 are formed in the fixing portion 31 of the plate 3 to screw the plate 3, multiple vertical slits that extend in the vertical direction may be formed at intervals in the longitudinal direction of the plate 3, instead of the through-holes 32, in order to make the plate 3 easier to curve in its entirety.

When multiple through-holes 32 are formed in the plate 3, it is not necessary to equalize the diameter of all of the through-holes 32. The diameter of the through-holes 32 may be changed as appropriate according to their roles. For example, when the diameter of one through-hole 32 is set to a size suitable for passing the connector 11 of the intramedullary nail 32 and the connector 11 is passed through this through-hole 32, the plate 3 does not interfere with the connector 11 even if the installation position of the fixing portion 31 is at the trochanter 103, which is located above the lower trochanter 108, rather than at the lower trochanter 108, which is located below the trochanter 103 shown in FIG. 10. This can reduce the size of the skin incision to be made to insert plate 3 into the body.

Next, the procedure for the surgical operation (osteosynthesis) for a femoral trochanteric fracture using the treatment tool 1' according to the second embodiment shown in FIGS. 10 and 11 is briefly described. First, the plate 3 is inserted into the body through an incision in the vicinity of the lateral surface of the trochanter 103 using forceps, or by hand. While widening the plate 3, the pressing portion 30 is positioned in the vicinity of the intertrochanteric crest 106 on the posterior surface of the trochanter 103, and the pressing portion 30 is brought into contact with the posterior surface of the trochanter 103 by a restoring force generated by deformation of widening the plate 3. The fixing portion 31 is then fixed to the main bone 105 with a screw 33 at the lateral portion of the lower trochanter 108, which is located below the trochanter 103 of the femur 100. Alternatively, a portion of the plate 3 other than the fixing portion 31 may be screwed to the femur 100. For example, the pressing portion 30 may be fixed to the posterolateral bone fragment 104 using a screw 33. The plate 3 may be widened by opening the pressing portion 30 using an appropriate instrument, or may be naturally widened by pressing the pressing portion 30 deeply to open the pressing portion 30 in conformity with the surface shape of the trochanter 103.

After the plate 3 is installed, the intramedullary nail 10 is implanted. The description of the procedure of implanting the intramedullary nail 10 is omitted because it is the same as that of the first embodiment.

According to the therapeutic apparatus 1' of the second embodiment, when the plate 3 is installed on the femur 100, the pressing portion 30 presses the posterolateral bone fragment 104 against the main bone 105 by a restoring force generated by deformation of widening the plate 3; accordingly, when a posterolateral bone fragment 104 is separated from the main bone 105 due to a defect of the trochanter 103, a surgery with the intramedullary nail 10 during osteosynthesis and bone fusion after osteosynthesis can be performed in a stable state such that the posterolateral bone fragment 104 is fixed to the main bone 105. Accordingly, since the defective posterolateral bone fragment 104 can be fixed to the main bone 105 by the plate 3 during the implementation of the intramedullary nail 10, the posterolateral bone fragment 104 can be maintained in the restored position during the period from before implantation of the intramedullary nail 10 until completion of the implantation; and there is no need to use forceps for temporary fixation. Further, since the risk of complications such as bone head rotation and prolonged fusion associated with a posterolateral defect can be reduced during bone fusion, femoral trochanteric fractures can be treated satisfactorily. Furthermore, since a defective posterolateral bone fragment 104 can be fixed to the main bone 105 without separation from each other until the posterolateral bone fragment 104 is joined to the main body 105, the restored position can be satisfactorily maintained without hindering the fusion of the posterolateral bone fragment 104 and the main body 105.

Since the treatment tool 1' according to the second embodiment can be attached to the femur 100 independently from the intramedullary nail 10 without interference with the intramedullary nail 10, which is an existing instrument for treating femoral trochanteric fractures, the treatment tool 1' can be attached to the position intended by the practitioner; and can also be used in combination with the existing intramedullary nail 10.

Figure 13:
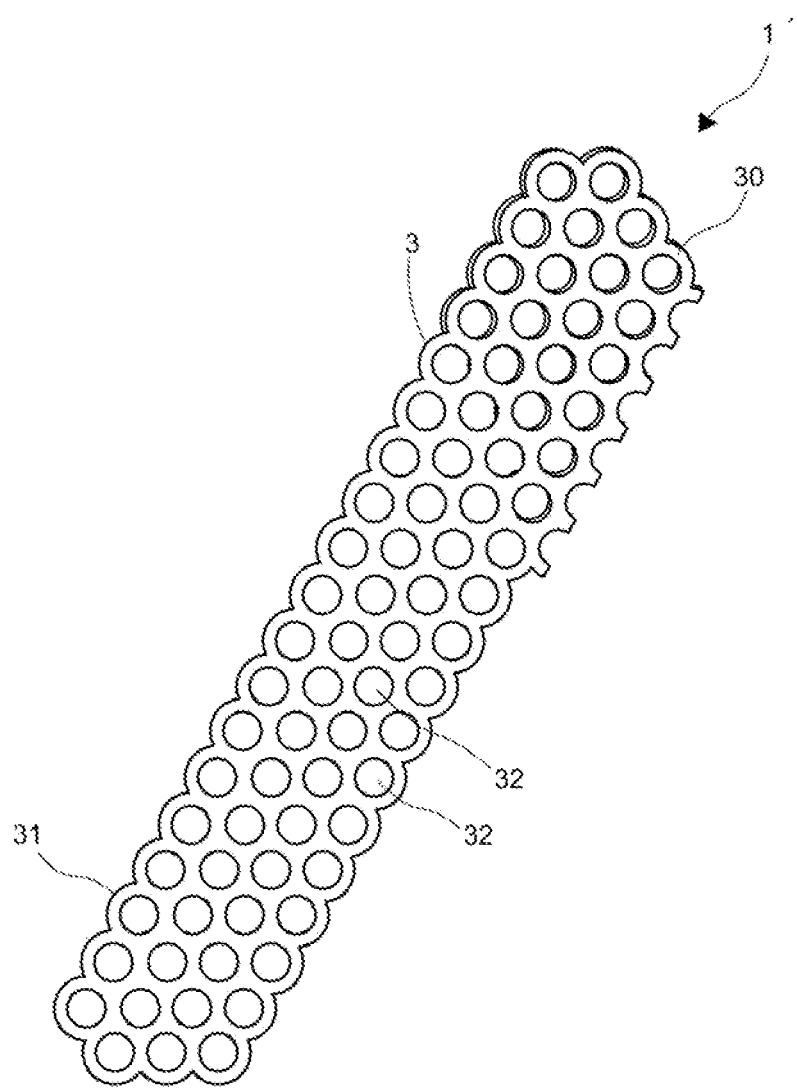
FIG. 13 is a side view showing a state before the treatment tool according to a modification example of the second embodiment is curved.

In the treatment tool 1' of the second embodiment, the plate 3 has a contour that is bent diagonally upward from a midway in the longitudinal direction. However, the plate 3 may have a contour that extends long in one direction, as shown in FIG. 13. As shown in FIGS. 10 and 11, the size of the skin incision to make to insert the treatment tool 1' into the body can be reduced if the plate 3 has a contour that is bent diagonally upward from a midway in the longitudinal direction.

In the treatment tool 1' according to the second embodiment, one end portion of the plate 3 in the longitudinal direction is folded back on itself to make the pressing portion 30 thicker than at least a portion of the other portions of the plate 3. Alternatively, the plate 3 itself may be formed in such a manner that one end portion of the plate 3 in the longitudinal direction is formed to be thicker than the other portions of the plate 3, to thereby increase the force of pressing the posterolateral bone fragment 104 by the pressing portion 30 against the main bone 105. The thickness of the pressing portion 30 does not necessarily have to be greater than the thickness of the other portions of the plate 3.

In the treatment tool 1' according to the second embodiment, as shown in FIG. 10, the plate 3 is placed below the connector 11 of the intramedullary nail 10 relative to the femur 100. However, for example, like plate 2 shown in FIG. 2, the plate 3 may be placed above the connector 11 and the auxiliary connector 15 of the intramedullary nail 10 with respect to the femur 100, i.e., the plate may be placed in such a manner that it extends from the back of the trochanter 103 of the femur 100 to the front of the trochanter 103 by passing around the greater trochanter. Alternatively, the plates 3 may be placed both above and below the connector 11 of the intramedullary nail 10 with respect to the femur 100.

In the treatment tools 1 and 1' according to the embodiments described above, the plates 2 and 3 have a curved shape formed by being bent beforehand. Alternatively, the plates 2 and 3 may initially have a flat plate-like shape and be bendable so as to have a curved shape in conformity with the surface configuration of the trochanter 103 of the femur 100.

The treatment tools 1 and 1' according to the embodiments described above are used for the treatment of femoral trochanteric fractures. These treatment tools can also be used for the treatment of femoral subtrochanteric fractures. Further, these instruments can also be used to treat a wide variety of long bone fractures, such as proximal humerus fractures and long bone diaphysis fractures.

DESCRIPTION OF REFERENCE NUMERALS 1,1': Treatment tool
2: Plate
20: Pressing portion
21: Hook
23: Second pressing portion
24: Hook
3: Plate
30: Pressing portion
32: Through-hole

The invention claimed is:

1. A treatment tool for use in treatment of a long tubular bone fracture, comprising:
   an elastic plate that has a curved shape having a curvature along the width direction or that is capable of being bent to the curved shape having the curvature along the width direction, the plate comprising at least one first pressing portion configured to press a fractured portion of a bone from one side by a restoring force that is generated by deformation of the plate to widen the curvature of the plate, and the plate comprising at least one second pressing portion configured to hold the fractured portion with the at least one first pressing portion;
   wherein the at least one first pressing portion defines a distal end of the plate in the width direction of the plate;
   wherein the at least one second pressing portion defines another distal end of the plate in the width direction;
   wherein the plate comprises a pair of first arms and a pair of second arms; the first arms are provided at intervals in a height direction orthogonal to the width direction of the plate, and the second arms are provided at intervals in the height direction orthogonal to the width direction of the plate, and
   wherein a distal portion of each first arm of the pair of first arms defines each of the at least one first pressing portions, and a distal portion of each second arm of the pair of second arms defines each of the at least one second pressing portions, the distal end of each of the at least one first pressing portions defining a first inwardly projecting hook and the distal end of each of the at least one second pressing portions defining a second inwardly projecting hook;
   wherein the first inwardly projecting hook of the at least one first pressing portion extends inwardly at more than 90° with respect to an extending direction of the first arms; and
   wherein the first inwardly projection hook of the at least one second pressing portion extends inwardly at 90° or more than 90° with respect to an extending direction of the at least one second arm.

2. The treatment tool according to claim 1, wherein the plate is vertically symmetrical with respect to a central axis parallel to the width direction.

3. The treatment tool according to claim 1, wherein the plate has a longitudinal shape, and comprises at least one through-hole formed in at least one area other than said first pressing portion.

4. The treatment tool according to claim 3, wherein the plate has multiple through-holes.

5. The treatment tool according to claim 3, wherein said first pressing portion is thicker than at least a portion of the rest of the plate.

6. The treatment tool according to claim 3, wherein an upper-end edge of the plate is slanted downwardly from said at least one first pressing portion toward an opposite end portion in the longitudinal direction of the plate.

7. The treatment tool according to claim 1, which is for use in treatment of a femoral trochanteric fracture or subtrochanteric fracture, wherein the at least one first pressing portion is configured to press a trochanter of a femur from a posterior side by the restoring force.

8. The treatment tool according to claim 7, wherein the at least one second pressing portion presses the trochanter of the femur from an anterior side by the restoring force.

* * * * *